Figure 3:
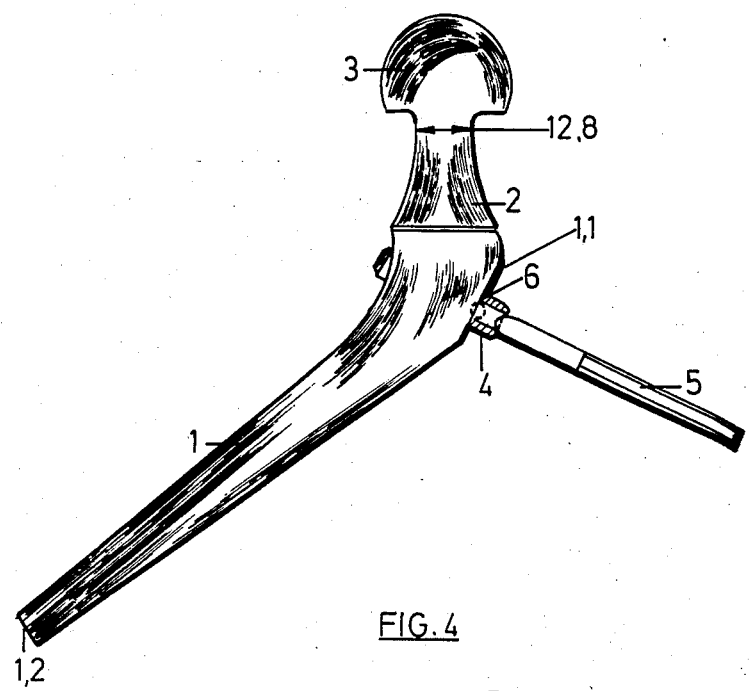

United States Patent [19]

Grobbelaar

[11] Patent Number: 4,605,416
[45] Date of Patent: Aug. 12, 1986

[54] APPARATUS FOR HIP ARTHROPLASTY

[75] Inventor: Charl J. Grobbelaar, Transvaal, South Africa

[73] Assignee: Arthroplasty Research & Development (Pty) Ltd., Pretoria, South Africa

[21] Appl. No.: 636,684

[22] Filed: Aug. 1, 1984

[30] Foreign Application Priority Data

Aug. 18, 1983 [ZA] South Africa ............... 83-3562

[51] Int. Cl.[4] ................... A61F 2/36; A61F 5/04
[52] U.S. Cl. ............................. 623/23; 128/92 B; 128/92 C
[58] Field of Search ............... 3/1, 1.9, 1.91, 1.911, 3/1.912, 1.913; 128/92 B, 92 BC, 92 C, 92 CA, 92 D

[56] References Cited

U.S. PATENT DOCUMENTS

| | | | |
|---|---|---|---|
| 3,924,275 | 12/1975 | Heimke et al. | 3/1.912 |
| 4,012,796 | 3/1977 | Weisman et al. | 128/92 C |
| 4,153,953 | 5/1979 | Grobbelaar | 3/1.913 |

FOREIGN PATENT DOCUMENTS

| | | | |
|---|---|---|---|
| 2548077 | 5/1977 | Fed. Rep. of Germany | 3/1.913 |
| 2754352 | 5/1979 | Fed. Rep. of Germany | 128/92 C |
| 2295730 | 8/1976 | France | 3/1.913 |

Primary Examiner—Richard J. Apley
Assistant Examiner—David J. Isabella
Attorney, Agent, or Firm—Fred Wiviott

[57] ABSTRACT

For use in hip arthroplasty procedures there is provided a femoral prosthesis and a separate greater trochanter fixation device which may optionally be used together depending on the approach selected by the surgeon. The fixation device is a stirrup and u-bolt and the stem of the femoral prosthesis may be grooved to receive the fixation device.

4 Claims, 5 Drawing Figures

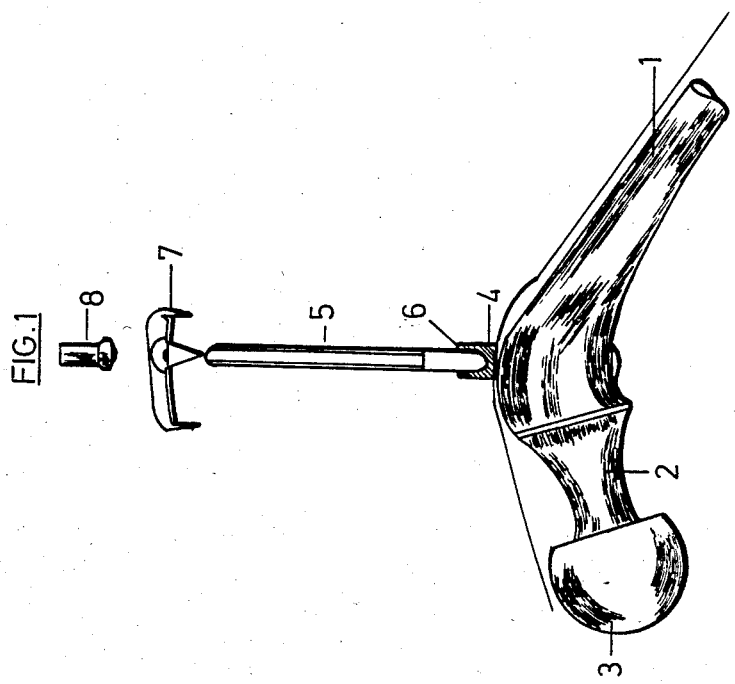
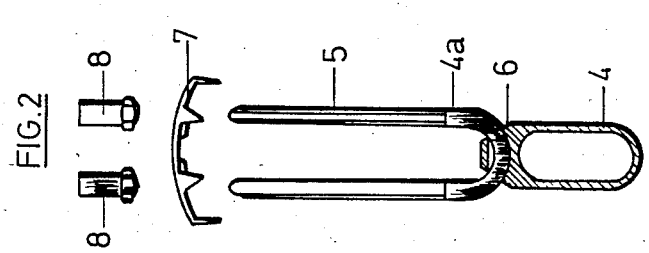

APPARATUS FOR HIP ARTHROPLASTY

This invention concerns improvements in and relating to apparatus for hip arthroplasty, in particular prosthetic devices for use in hip arthroplasty procedures.

In hip arthroplasty procedures the selection of the type of femoral prosthesis which is employed is dictated by the operational procedure, in particular the approach to the joint. The operational procedures in hip arthroplasty broadly can be divided into the kind which requires the removal of the greater trochanter and thereafter its replacement and fixation on the one hand (the Charnley procedure), and the kind which do not require the removal of the greater trochanter, on the other hand, (the Muller procedure). In the former kind of operative procedure it is preferred by many surgeons to select a femoral prosthesis which is adapted to make possible a very secure trochanter fixation. An example of a u-bolt trochanter fixation is described in patent No. 77/1690, in accordance with which the prosthesis stem has a hole through which the u-bolt is passed. In other examples of this procedure wire binding is resorted to for fixation of the greater trochanter.

The inventor has thus perceived that it is desirable to provide femoral prosthetic devices which are adaptable to use in either category of procedure according to the preference or selection of the surgeon.

A femoral prosthetic device for use in hip arthroplasty in accordance with this invention comprises a stem, a neck and either a peg for a ceramic ball, or an integral ball, for use in combination with an acetabular prosthesis and adapted for use optionally in combination with a greater trochanter fixation device comprising preferably a stirrup and u-bolt, in general a sling, ring or similar fixation element(s) which can be passed over or otherwise attached to the stem without perforating the stem.

The stirrup and u-bolt may be two parts, the u-bolt swingable in a hole in the stirrup, with advantage. However, the invention includes also an integral stirrup cum u-bolt. In all cases a good, close fit between the stirrup and the stem of the femoral prosthesis is preferred.

The invention extends also to the combination comprising a femoral prosthetic device with the greater trochanter fixation device.

Finally, the invention extends to the greater trochanter fixation device comprising a stirrup and u-bolt or other fixation element(s) and adapted for fitting to any femoral prosthesis comprising a stem, neck and ball.

The stem, neck and ball can be provided in ranges of dimensions and proportions to permit selection of appropriate kinds for each particular case.

The stem of the femoral prosthesis may be grooved to receive the greater trochanter fixation device so that the latter may approach closer to the stem. The stem is preferably formed so as to provide a secure lodgement position of the stirrup or similar on the stem.

The skeleto-prosthetic interfaces can with advantage be coated with an inert material such as a ceramic, especially an alumina ceramic. This coating can be coarse textured for good bonding.

Similarly the acetabular cup can be provided, if not in a suitable polymer, then in a ceramic such as a high purity alumina which will then be given a very high polish on the surfaces mating with the ball.

Especially where a stainless steel is used for the femoral prosthesis, for example, and also quite generally, care must be given to avoiding any form of electro-chemical attack between the greater trochanter fixation device. With stainless steels crevice corrosion effects must be suppressed, for example, by a coating, e.g. plastic or ceramic on the stirrup and u-bolt or similar. Where the femoral stem has a ceramic coating this may serve this purpose.

Figure 4:
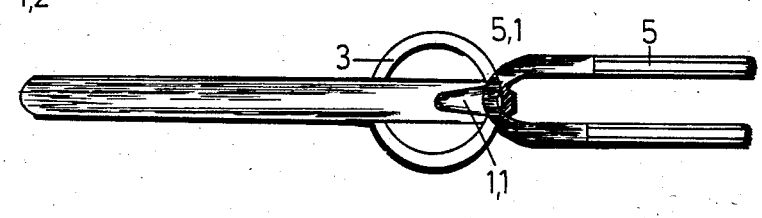
Figure 5:
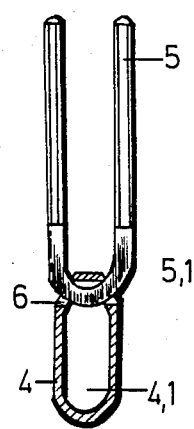

This invention will now be more fully described by way of an example with reference to the drawings in which two preferred embodiments are shown, FIGS. 1 and 2 show a first embodiment, and FIGS. 3, 4 and 5, a second embodiment.

As shown in FIGS. 1 and 2 of the drawings the prosthetic device comprises a stem 1, a neck 2 and a ball 3 which may in principle either be a ceramic ball fitted on a peg at the end of the neck 2 or an integral ball. This device is provided in combination with a trochanter fixation implement which is adapted for optional attachment to the femoral prosthesis. The trochanter fixation element comprises a stirrup 4 in which a u-bolt 5 is pivotally fixed by passing through a hole 6 in the stirrup 4. The u-bolt 5 has a clamping plate 7 and nuts 8 for securement.

The stem 1 may be specially adapted to provide a niche or other lodgement position for the stirrup into which the stirrup can settle when it is in use and the nuts tightened up to provide a secure fixation of the greater trochanter.

In a similar manner to the femoral prosthesis the greater trochanter fixation device can also be coated with a biocompatible material such as a high purity alumina ceramic.

With this device the femoral prosthesis can be used alone in a procedure which the surgeon may select in which he does not wish to use the greater trochanater fixation device comprising the stirrup and u-bolt. Alternatively, the same femoral fixation device can also be used in a procedure in which the surgeon selects the use of the greater trochanter fixation device.

Where a range of sizes and proportions of the femoral fixation device is provided an analogous range of greater trochanter fixation implements can also be provided as required.

The stirrup will also be dimensioned and proportioned to facilitate fixation in the truncated femur with the stirrup set into the surrounding cancellous bone.

The stirrup can also be provided with the head part of the stirrup 4a through which the hole 6 passes split in such a manner that the tensioning of the u-bolt 5 will tend to close the head of the stirrup closing the slit 4a in a manner which will tighten the stirrup in its position over the stem 1.

The materials for the stirrup may, equally as in the case of the femoral prosthetic component, be suitable high alloy steels such as are used in hip arthroplasty prosthetic components.

Alternatives for the u-bolt could be straight bolts or other suitable fasteners.

As shown in FIGS. 3 and 4 a similar stirrup and u-bolt may be provided for the femoral prosthesis and the same reference numerals have been accordingly used for the similar parts and reference is made to the description thereof above. In this case, however, the stem 1 of the femoral prosthesis is grooved at 1,1 to receive the arched part 5,1 of the u-bolt 5 so that this part 5,1 is partially recessed into the stem 1, the stirrup 4 for this case therefore has a hole 6 for the u-bolt 5 which breaks into the hole 4,1 for the stem. The location of the hole 6 then holds the portion 5,1 of the u-bolt 5 into the groove 1,1 of the stem when the stirrup 4 is passed over the stem to a position as shown, for example, in FIG. 3.

The lower or distal end 1,2 of the stem 1 is squared off as it is found this is more effective in pushing cement down to the lowest part of the hole in the femor which has been prepared for the stem.

This entirely integral femoral prosthesis may be provided in stainless steel 316L, the stem being sandblasted and the neck and head being polished. The femoral prosthesis may also be supplied in titanium, having a separate head of chrome cobalt alloy shrink fitted onto top end of stem.

Moreover preferably the head diameter is made to be larger than is usual, in fact 32 mm, so as to coincide with the head size of the currently used Muller femoral prosthesis so that this prosthesis can be used in a revision procedure applied to an old Muller implant.

A preferred feature of this embodiment of the invention is that the angle which lies between the axis of the head and neck and the axis or one side of the stem is less than is usual, in fact 48° so as to reduce the stresses on the femoral prosthesis which are related to this angle and thereby reduce the incidence of failures in this respect.

Preferably, that part of the u-bolt which passes through the hole in the stirrup is covered with a silicon polymer or a ceramic so as to insulate the metal of the u-bolt from the metals of the stirrup and of the stem with a view to preventing electrochemical attack at region of contact such as crevice corrosion.

It will be appreciated that the prosthesy shown in the drawings leave the decision in the course of surgery to be taken by the surgeon as to whether the prosthesis shall be used with or without the greater trochanter fixation device. Thus the surgical approach and the option of greater trochanter removals are not restricted by this prosthesis.

The femoral prosthesis may be provided in a range of sizes, for example, extra heavy, heavy and standard, etc. implying a variation in the dimensions of the stem. Where this is the case preferably, the stirrup is varied so as to suite the stem size and in preferred embodiments it may be regarded as critical that the stirrup has a very close and good fit with the stem. Preferably, the increasing dimensions of the stem as it approaches the neck are such that the stirrup can be wedged firmly in position. The stirrup can be provided in titanium where the stem is stainless steel so as to avoid crevice corrosion effects. The stem could alternatively be provided in a chromed cobalt alloy.

An acetabular cup with which this prosthesis is used could be provided in a high density polyethylene. However, a ceramic acetabular cup offers improved properties in many respects, but is much more expensive.

I claim:

1. The combination of a femoral prosthetic device for use in hip arthroplasty and a greater trochanter fixation device, said femoral prosthetic device comprising a stem, a neck and a ball for use in combination with an acetabular prosthesis, the stem, neck and ball of the femoral prosthetic device being unperforated, said greater trochanter fixation device comprising a loop part and a u-bolt, said loop part having a ring-like portion constructed and arranged to be passed over and thereby attached to the stem without perforating the same, the loop part having a hole formed therein through which the u-bolt passes unhindered, said u-bolt being swingable in said hole, the loop part and the stem being mutually contoured such that the loop part is adopted to snugly embrace the stem.

2. The femoral prosthetic device set forth in claim 1 wherein the stem of the femoral prosthesis has a groove formed thereon for receiving the ring-like portion of the loop part thereon.

3. A greater trochanter fixation device for use in hip arthroplasty with an unperforated femoral prosthetic device having a stem, a neck and a ball, said fixation device comprising a loop part and u-bolt, the loop part being ring-like in form and constructed and arranged to be passed over and attached to the stem of the femoral prosthetic device without perforating the stem, the neck or the ball thereof, a hole formed in the loop part and sized relative to said u-bolt so that the u-bolt is received unhindered in said hole and is swingable therein, the loop part being constructed and arranged for snugly embracing the stem.

4. The greater trochanter fixation device as claimed in claim 3 wherein the u-bolt has an insulating coating on the portion thereof which passes through the hold in the loop part.

* * * * *